United States Patent [19]
Cheng

[11] Patent Number: 6,060,033
[45] Date of Patent: May 9, 2000

[54] PROCESS FOR REMOVING HCL FROM HYDROCARBON STREAMS

[75] Inventor: Linda Shi Cheng, Rolling Meadows, Ill.

[73] Assignee: UOP LLC, Des Plaines, Ill.

[21] Appl. No.: 09/064,589

[22] Filed: Apr. 22, 1998

[51] Int. Cl.[7] .............................. C07C 7/12; B01D 53/02
[52] U.S. Cl. .......................... 423/240 S; 95/131; 95/132; 585/823
[58] Field of Search ................. 95/131, 132; 426/240 S, 426/240 R; 585/823

[56] References Cited

U.S. PATENT DOCUMENTS

| | | | |
|---|---|---|---|
| 3,551,093 | 12/1970 | Myers et al. | 423/420.2 |
| 3,557,025 | 1/1971 | Emerson et al. | 423/419.1 |
| 4,579,839 | 4/1986 | Pearson | 423/628 |
| 4,639,259 | 1/1987 | Pearson | 95/132 |
| 4,762,537 | 8/1988 | Fleming | 95/132 |
| 5,316,998 | 5/1994 | Lee | 502/415 |
| 5,505,926 | 4/1996 | Lee et al. | 423/240 R |
| 5,620,589 | 4/1997 | Yan | 95/131 |

*Primary Examiner*—Steven P. Griffin
*Assistant Examiner*—Peter DiMauro
*Attorney, Agent, or Firm*—John G. Tolomei; Richard P. Silverman

[57] ABSTRACT

The invention relates to a process for removing hydrogen halides from hydrocarbon-containing streams. More particularly, the invention relates to a process and an HCl sorbent for the removal of HCl and other hydrogen halides from hydrocarbon streams to prevent the formation of green oils. The sorbent has an increased capacity for the sorption of HCl and a reduced catalytic activity for the formation of green oils which, surprisingly, results from the pre-loading of water on a sodium promoted alumina adsorbent. The pre-loading of water on the sodium promoted alumina adsorbent in the range of about 5 to about 11 percent of the essentially water-free adsorbent increases the HCl sorption capacities by about 25% with a corresponding decrease in catalytic reactivity.

5 Claims, No Drawings

PROCESS FOR REMOVING HCL FROM HYDROCARBON STREAMS

FIELD OF THE INVENTION

The present invention relates to a method for treating hydrocarbon streams to remove acid gases. More particularly, the present invention relates to a process using a catalytically inert sorbent for removing HCl from hydrocarbon-containing streams.

BACKGROUND OF THE INVENTION

Acid gases are present as impurities in numerous industrial fluids, i.e., liquid and gas streams. These acid gases include hydrogen halides such as HCl, HF, HBr, HI and mixtures thereof. For example, one of the key processes in refining petroleum is catalytic reforming. In the catalytic reforming process, a light petroleum distillate or naphtha range material is passed over a noble metal catalyst to produce a high octane product. Hydrogen is a by-product of the catalytic reforming process, and a portion of the by-product hydrogen is recycled to the reaction zone to maintain catalyst stability. Typically, the noble metal reforming catalyst is promoted with chloride which, in the presence of hydrogen, results in the production of a small amount of hydrogen chloride. Thus, the net by-product hydrogen withdrawn from the catalytic reforming process generally contains a small amount of hydrogen chloride. Similarly, in a process for the dehydrogenation of light isoparaffins to produce isoolefins, the promoting of the noble metal catalyst with chloride will produce a net hydrogen stream containing small amounts of HCl. The net hydrogen produced in the catalytic reforming process and the dehydrogenation process is generally used in sensitive downstream catalytic processes. In addition, there are other hydrocarbon and chemical processes in which small amounts of HCl are generated and carried away in gas or liquid streams. Even small amounts of gaseous HCl present in the net hydrogen can seriously interfere with the operation of downstream processes which use the hydrogen and can cause corrosion problems in the equipment such as pipes, valves, and compressors which convey hydrogen. Generally, HCl in gas or liquid hydrocarbon streams must be removed from such streams to prevent unwanted catalytic reactions and corrosion to process equipment. Furthermore, HCl is considered a hazardous material and releasing the HCl to the environment must be avoided.

Currently, activated alumina is the most widely used sorbent in the petroleum refining and chemical industries. Activated alumina is employed as a scavenger for the removal of small quantities of HCl from fluid streams. Significant developments to improve the performance of alumina to remove HCl from hydrocarbon streams are disclosed in U.S. Pat. Nos. 4,639,259 and 4,762,537 which relate to the use of alumina-based sorbents for removing HCl from gas streams. U.S. Pat. Nos. 5,505,926 and 5,316,998 disclose a promoted alumina sorbent for removing HCl from liquid streams by incorporating an alkali metal oxide such as sodium in excess of 5% by weight on to an activated alumina base. It is also known that alumina can be promoted to sorb more HCl by impregnating the alumina with sodium carbonate or sodium hydroxide or calcium hydroxide. U.S. Pat. No. 4,639,259 discloses the use of calcium acetate to improve the dispersion of the calcium oxide on the alumina to achieve higher sorption capacity. The use of promoted alumina compared to other alumina-based sorbents can extend the length of time a fixed amount of sorbent will sorb HCl. By increasing the content of promoters such as sodium carbonate or sodium hydroxide, the HCl sorption capacity of the scavenger can be increased. However, the addition of promoters to alumina to improve the capacity of the sorbent for HCL appears to have a point of diminishing returns. Despite the type and amount of promoter incorporated into the alumina-based and promoted alumina materials, commercial experience shows that alumina-based and promoted alumina sorbents have a relatively low capacity for the sorption of HCl, often limited to levels less than 10–16 wt-% HCl.

Existing sorption processes for removing HCl from hydrocarbon-containing streams typically involve passing the hydrocarbon-containing fluid stream over the sorbent, which is disposed in a fixed bed. Conventionally, these fixed beds contain alumina-based sorbents wherein sodium or calcium is doped or coated on the alumina. Typically, the alumina-based and promoted alumina materials are formed into nodules or spheres. As the alumina-based sorbents pick up HCl, the sodium or calcium promotor, as well as aluminum, reacts with HCl to form chloride salts. Because HCl molecules are able to form hydrogen bonds with chloride ions, a limited amount of HCl can become physically sorbed on the surface of the salt molecules. However, the alumina sorbent in this service is known to have the undesirable property of converting certain hydrocarbons in the streams into a substance often called "green oil" which often collects in the fixed sorbent bed. Typically, these green oils are green or red in color. They generally contain chlorinated $C_6$–$C_{18}$ hydrocarbons and are believed to be oligomers of light olefinic hydrocarbons. The presence of green oils in the fixed sorbent bed fouls the sorbent bed and results in the premature failure of the sorbent. When this fouling occurs, often costly measures are required to remove the spent sorbent from the bed. Furthermore, the chloride content of the green oils on the spent sorbent makes disposal of the spent sorbent an environmental problem. While the exact mechanism of green oil formation is unknown, it is believed that green oils are formed by catalytic reaction of aluminum chloride or HCl with the hydrocarbon resulting in a chlorinated hydrocarbon. Since both aluminum chloride and free HCl are known to be acidic and present on the surface of the sorbent, they are able to catalyze the polymerization of reactive hydrocarbons. Since it is very difficult to avoid the physical sorption of HCl and the formation of chloride salts on alumina-based and promoted alumina sorbents, the catalyzed polymerization reaction of hydrocarbon and the formation of green oil is not easily avoided. Green oil formation remains an unresolved industry problem during the removal of HCl from hydrocarbon streams.

When unsaturated hydrocarbons such as butadiene or other olefinic compounds are present in a hydrocarbon-containing stream, these compounds can be polymerized on acidic surfaces. Alumina based sorbents and promoted alumina sorbents, once they adsorb HCl, become acidic during the sorption process, and thus, acquire catalytic activity for the polymerization of the reactive hydrocarbons in the stream. When green oils are produced during the HCl sorption process, the spent sorbent represents a costly disposal problem. The formation of these polymers fouls the sorbers, shortens sorbent life, and creates a problem for the disposal of the solid adsorbents now containing chlorinated hydrocarbons. Since an HCl sorbent is not regenerable, the treatment of streams with even moderate to high HCl content, such as an HCl sorbent with a capacity of 10–16 wt-%, requires the fixed bed of sorbent to be changed frequently and imposes a downtime on the upstream process. Because the change of sorbent beds containing polymerized hydrocarbons requires costly measures to dig the sorbent out of the sorbent bed, the loss of production time and the maintenance costs are especially significant. The polymerization or acidic reactivity of the Cl loaded adsorbents must be reduced to avoid these problems.

There are many compounds that are reactive to acid gases such as hydrogen halides which can be employed as a scavenger sorbent to remove trace amounts of acid gases from fluid streams. However, for a compound to function in a fluid stream from a process plant where hydrocarbons are present, the material must have good acid gas sorption capacity, have sufficient physical strength, and be catalytically inert in the presence of reactive hydrocarbons. That is, the compound should have a reduced catalytic activity. By a reduced catalytic activity, it is meant that the catalytic activity is about ⅓ to ½ that of the catalytic activity of the conventional sodium promoted alumina.

It is an objective of the present invention to provide a sorbent which is effective for removing HCl from hydrocarbon streams and which is catalytically inert to reaction of those hydrocarbons to form the green oils.

It is an objective of the present invention to provide a sorbent for removing HCl from a hydrocarbon stream with an improved capacity for sorption of HCl with a minimum requirement for maintenance costs.

It is objective of this present invention to provide a sorbent which avoids the production of potentially hazardous chlorinated hydrocarbons.

SUMMARY OF THE INVENTION

Surprisingly, it was discovered that pre-loading water on the sodium promoted alumina adsorbent increased the HCl adsorption capacity by approximately 25% and that the reactivity for polymerization was surprisingly decreased by about 80% (as measured by the 1,3-butadiene reactivity test.) In actual commercial applications, this significant decrease of reactivity may translate to an even higher Cl loading capacity at a lower unit cost for the adsorbent, thereby extending adsorbent life and minimizing emergency shutdowns from increased pressure drop or adsorbent bed plugging.

The sorbents of the present invention exhibit a low catalytic activity for hydrocarbon polymerization and a high HCl sorption capacity. Since the physical sorption of HCl is generally thought to be a surface phenomenon and the presence of HCl on the surface of the sorbent would tend to catalyze the polymerization of hydrocarbon, it is surprising that the HCl sorbents of the present invention show such a low catalytic activity. Surprisingly, it was found that the alumina promoted adsorbents—when pre-loaded with a critical amount of water—exhibited an improved HCl adsorption capacity and reduced catalytic activity for the formation of polymers or green oils and displayed a much higher overall sorption capacity than the adsorbents of the prior art. According to the present invention, a process is provided for treating a hydrocarbon stream comprising hydrocarbons and a hydrogen halide. In order to remove the hydrogen halide from the hydrocarbon stream, the hydrocarbon stream is contacted with a sorbent comprising an alumina-containing material impregnated with at least 3% by weight of an alkali metal oxide based on the weight of alumina present and wherein the sorbent comprises from about 5 to about 11 percent water based on the weight of essentially water-free sorbent to provide a sorbent having a reduced catalytic activity to form green oils from said hydrocarbons. Preferably, the essentially water-free basis of the sorbent corresponds to an LOI at 950° C. of less than about 5 wt %.

DETAILED DESCRIPTION OF THE INVENTION

To measure the catalytic reactivity of the sorbent for hydrocarbons, 1,3-butadiene was used as the reactant. The sorbent was first loaded with HCl by exposing the sorbent to HCl gases. The unsorbed HCl was removed and the now HCl loaded sorbent was exposed to 1,3-butadiene. For those sorbents that are not catalytically active, 1,3-butadiene was only physically sorbed. For catalytically active sorbents, the sorption of 1,3-butadiene resulted in the production of $C_{12}$ or larger molecules. These heavy molecules formed a liquid phase (not sorbed) on the surface of solid sorbent. Surprisingly, the water pre-loaded sorbents had much lower catalytic activity than the alumina promoted sorbents which were not pre-loaded. To put the degree of pre-loading on a definite basis, we introduce the term "loss on ignition". The term loss on ignition (LOI) means the loss which results from heating a sample of adsorbent using an ignition temperature of 950° C. Typically, water and other volatile components such as chlorine or fluorine, which are generally found in the adsorbent, are driven off at this temperature and are included in the LOI. The LOI is determined by placing a weighed sample of the adsorbent in a crucible and heating the crucible to a temperature of about 950° C. for about 1 hour. The material evolved during the heating of the sample is analyzed by conventional methods to determine a base water content and the content of the other volatile components. After cooling, the adsorbent sample is weighed again and the mass loss is calculated as a mass-percent loss on ignition. Thus, the essentially water-free basis of the adsorbent is the weight of the sample, less the water portion of the LOI at 950° C. For example, a typical sample of promoted alumina was found to have an LOI of about 3.4 wt %, wherein 1.9 wt-% was water and 1.5 wt-% was determined to be other volatile components. For the purposes of this application, water contents are expressed in terms relative to an essentially water-free basis.

A commercial version of 8% $Na_2O$ promoted alumina has an HCl capacity of 12.9% and 1,3-butadiene reactivity of 5.7%. By gradually increasing the amount of water pre-loaded on the adsorbent, a steady increase in HCl adsorption capacity and a steady decrease in 1,3-butadiene reactivity was observed with a water pre-loading of from about 5 to about 11 weight percent of the adsorbent relative to the adsorbent on an essentially water-free basis. At a water loading above about 11%, the reactivity and HCl capacity began to decrease, indicating the critical range over which this surprising advantage results. More preferably, the water loading comprises from about 7 to about 8.5 weight percent of the adsorbent on a dry basis. At this water loading level, the HCl capacity increased about 25% and the 1,3-butadiene reactivity decreased about 80% compared to the commercial 8% $Na_2O$ promoted adsorbent. The HCl loading was also verified by chloride chemical analysis, and the results matched well with McBain results as indicated in the following table by corrected Cl wt %.

Experimental results showed the effect of pre-loading the promoted alumina adsorbent. It is believed that the water possibly hydrates the $Na_2O$ or $NaAlO_2$ for NaOH on the surface of the adsorbent which is a stronger base. The stronger base appears to explain the increase in HCl capacity. It is believed that the decrease in 1,3-butadiene reactivity results from better NaOH re-dispersion on the surface of the adsorbent or the blocking of alumina sites. It appears that exposed alumina surface sites contribute to the olefin reactivity when these sites are loaded with HCl. By improving the disbursement of the $Na_2O$ on the surface and by covering the alumina sites on the surface of the adsorbent, an increase in the HCl capacity and a reduction in catalytic reactivity results.

EXAMPLES

To more fully illustrate the invention, the following examples are presented.

The equilibrium HCl adsorption capacity of promoted alumina was evaluated in a conventional McBain Bakker Balance. A detailed description of this device, in general, can be found in text books such as "Physical Adsorption of Gases" by D. M. Young and A. D. Crowell, Butterworths, 1962, hereby incorporated by reference. A series of approximately 1 gram each of samples a-f adsorbents were preloaded as described hereinbelow with water at the level shown in Table 1 and activated through vacuum evacuation at room temperature for a period of about 12 hours until the vacuum reached at least $1.3 \times 10^{-3}$ kPa ($10^{-2}$ torr). HCl adsorption was carried out at an HCl partial pressure of about 0.665 kPa (5 torr) by exposing all of the samples to a gas containing HCL at 24° C. for about 24 hours. The samples were maintained at this HCl partial pressure for the duration of the procedure. HCl adsorption was monitored by recording the weight of each sample at different time intervals until the weight gains had stabilized. The final HCl loadings were verified by conventional chemical analysis for chloride content of the adsorbent samples. The chloride content reported in Table 1 is shown corrected by the residual chloride content in the fresh base. The chloride contents ranged from about 11.9 wt % for the "as received" a to about 17.2 wt % for the "as received" a with an additional 8.2 wt % pre-loaded water.

The water content of each adsorbent sample was determined via a standard Karl Fisher amperometry using a 701 Metrohm titrator unit. In this apparatus the titration compartment is attached to a glass tube which is heated by a horizontal tube furnace. Approximately 1 gram of adsorbent is used for each test. The test sample was heated to 950° C. in the presence of a nitrogen purge. The purge gas was bubbled through a solvent mixture (such as sold under the trademark "Hydranal"-Solvent, manufactured by Riedel-de-Haen) comprising methanol, imidazol, and sulfur dioxide which scrubbed and reacted with the moisture present. The water amount was determined by titration with a titrant (such as sold under the trademark "Hydranal"-Titrant/5, manufactured by Riedel-de-Haen) comprising methanol and iodine. LOI (Loss on Ignition) was obtained by the weight difference before and after the heating using an analytical balance. The difference between LOI and the determined water gives the non-aqueous volatile content of the sample. The level of water pre-loading was attained by exposing approximately the 1 gram samples of the adsorbent to a partial pressure of $H_2O$ vapor which would result in a particular water pre-loading prior to starting the HCl capacity testing. In the McBain measurement, 1 g of sodium promoted alumina is used for the testing. After loading the samples into the McBain, the adsorbents were activated through vacuum evacuation at room temperature for a period of about 12 hours. The samples were exposed to a specific water partial pressure by adjusting the temperature of liquid water between a temperature of from 0° C. to 24° C. to obtain the required partial pressure of water vapor. When the water loading for each sample reached equilibrium, the McBain tubes containing sample buckets were sealed in preparation for the HCl capacity test. The water pre-loading wt % was reported relative to the water content of the "as received" a adsorbent. The McBain manifold was evacuated and HCl gas was introduced as described herein above. HCl adsorption and 1,3-butadiene reactivity tests were then carried out with the pre-loaded adsorbents.

To further verify the HCl loading, conventional chloride chemical analysis of the adsorbent samples was conducted and the results showed that chloride loading in the McBain test correlates well with the analysis of chloride on the adsorbent. The "as received" sodium promoted alumina was found to have an LOI at 950° C. of about 3.4 wt % with a water content of about 1.9 wt-%.

TABLE 1

CHLORIDE CAPACITY AND REACTIVITY OF WATER LOADED ADSORBENT

| | | $H_2O$ Pre-Loading WT % | $H_2O$ Water-free Basis ° C. | HCl Capacity, WT % | 1,3 BUTADIENE REACTIVITY WT % | Cl Chemical Analysis. WT % | Cl Corrected WT % |
|---|---|---|---|---|---|---|---|
| a | | As rec'd | 1.9 | 12.9 | 5.7 | 9.7 | 11.9 |
| b | | 2.6 | 4.5 | 11.0 | 3.0 | 11.1 | 13.3 |
| c | | 5.3 | 7.2 | 14.1 | 2.2 | 10.3 | 13.1 |
| d | | 7.0 | 8.9 | 16.1 | 1.0 | 12.1 | 15.9 |
| e | | 7.6 | 9.5 | 15.9 | 0.9 | 12.0 | 15.9 |
| f | | 8.2 | 10.1 | 17.2 | 1.5 | 10.6 | 14.5 |

EXAMPLE II

Catalytic reactivity of the HCl loaded sodium promoted alumina samples from Example I was evaluated as follows. Following the HCl adsorption of Example I, the McBain system was evacuated briefly to remove essentially all residual HCl gas. Each of the samples was then exposed to 1,3-butadiene at a partial pressure of 13.3 kPa (100 torr) for 48 hours. For the catalytically active sorbent materials, the 1,3-butadiene reacted continually to form oligomers, which was reflected by the continued weight gain over exposure time. It was found that as the water content increased, the 1,3-butadiene reactivity decreased continuously. At 7.6% water loading, the reactivity had decreased about 80% compared to the "as received" a sodium promoted alumina.

We claim:

1. A process for the removal of hydrogen halide from a fluid hydrocarbon-containing stream comprising hydrogen, hydrocarbons, water and hydrogen halide, which process comprises contacting said fluid stream with a sorbent material in a packed bed, said sorbent having a reduced catalytic activity to form green oils from said hydrocarbons and comprising an alumina-containing material impregnated with at least 3% by weight of an alkali metal oxide based on the weight of alumina present and between 5 and about 11 percent base water based on the weight of the sorbent on an essentially water-free basis.

2. The process of claim 1 wherein said hydrogen halide is selected from the group consisting of hydrogen chloride, hydrogen fluoride, hydrogen iodide, hydrogen bromide and mixtures thereof.

3. The process of claim 1 wherein the fluid stream comprises a net hydrogen stream from a catalytic reforming process and said hydrogen halide is hydrogen chloride.

4. The process of claim 1 wherein the fluid stream comprises a net hydrogen stream from a light paraffin dehydrogenation process and said hydrogen halide is hydrogen chloride.

5. The process of claim 1 wherein the fluid stream comprises a net hydrogen stream from a light paraffin dehydrogenation process and said hydrogen halide comprises hydrogen chloride.

* * * * *